US006207819B1

(12) United States Patent
Manoharan et al.

(10) Patent No.: US 6,207,819 B1
(45) Date of Patent: Mar. 27, 2001

(54) COMPOUNDS, PROCESSES AND INTERMEDIATES FOR SYNTHESIS OF MIXED BACKBONE OLIGOMERIC COMPOUNDS

(75) Inventors: Muthiah Manoharan; Martin A. Maier, both of Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/250,075

(22) Filed: Feb. 12, 1999

(51) Int. Cl.$^7$ .................. C07H 21/00; C07H 31/70; C12P 19/34

(52) U.S. Cl. ................ 536/25.3; 536/22.1; 536/23.1; 536/25.31; 536/26.1; 536/27.1; 435/91.1

(58) Field of Search ............... 536/24.5, 243.1, 536/27.1, 26.7, 25.34, 24.3, 22.1, 25.3, 25.31; 435/5, 6, 91.1

(56) References Cited

U.S. PATENT DOCUMENTS

| Re. 34,069 | 9/1992 | Köster et al. ............. 536/25.3 |
| 3,687,808 | 8/1972 | Merigan et al. ............ 435/91.3 |
| 4,415,732 | 11/1983 | Caruthers et al. ........... 536/26.5 |
| 4,458,066 | 7/1984 | Caruthers et al. .......... 536/25.34 |
| 4,500,707 | 2/1985 | Caruthers et al. .......... 536/25.34 |
| 4,668,777 | 5/1987 | Caruthers et al. ........... 536/26.5 |
| 4,725,677 | 2/1988 | Köster et al. ............ 536/25.34 |
| 4,816,571 | 3/1989 | Andrus et al. ............. 536/25.3 |
| 4,973,679 | 11/1990 | Caruthers et al. .......... 536/26.71 |
| 5,132,418 | 7/1992 | Caruthers et al. ........... 536/25.3 |
| 5,149,798 | 9/1992 | Agrawal et al. ............. 536/25.3 |
| 5,212,295 | 5/1993 | Cook ...................... 536/26.7 |
| 5,541,307 * | 7/1996 | Cook et al. ............... 536/23.1 |
| 5,548,076 | 8/1996 | Froehler et al. ........... 536/25.34 |
| 5,670,633 | 9/1997 | Cook et al. ............... 536/23.1 |
| 5,760,202 * | 6/1998 | Cook et al. ............... 536/22.1 |

OTHER PUBLICATIONS

Stein et al. Physicochemical properties of phosphorothioate oligodeoxynucleotides. Nucleic Acids Research. vol. 16, No. 8, 1988, pp. 3209–3221.*

Altmann, K. et al., "Second Generation of Antisense Oligonucleotides: From Nuclease Resistance to Biological Efficacy in Animals," *Chimia*, 1996, 50, 168–176.

Altmann, K. et al., "Second Generation Antisense Oligonucleotides–Inhibition of Pkc– 1 And c–RAF Kinase Expression by Chimeric Oligonucleotides Incorporating 6– Substituted Carbocyclic Nucleosides and 2'–O–Ethylene Glycol Substituted Ribonucleosides," *Nucleosides & Nucleotides*, 1997, 16(7–9), 917–925.

Altmann, K. et al., "Second–Generation Antisense Oligonucleotides: Structure– Activity Relationships and the Design of Improved Signal–Transduction Inhibitors", *Biochem. Soc. Trans.*, 1996, 24, 630–637.

Alul, R.H. et al., "Oxalyl–CPG: a labile support for synthesis of sensitive oligonucleotide derivatives", *Nucl. Acid Res.*, 1991, 19, 1527–1532.

Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells", *J. Biol. Chem.*, 1997, 272, 11994–12000.

Beaucage, S.L. et al., "Advances in the Synthesis of Oligonucleotides by the Phosphoramidite Approach", *Tetrahedron*, 1992, 48, 2223–2311.

Bielinska, A. et al., "Regulation of Gene Expression with Double–Stranded Phosphorothioate Oligonucleotides", *Science*, 1990, 250, 997–1000.

Bizdena et al., "Synthesis and Properties of 2'–O–Methoxymethyl Oligonucleotides", *Collect. Czech. Chem. Commun.*, 1996, 61–S283–S286.

Brown, T. et al., "Modern machine–aided methods of oligodeoxyribonucleotide synthesis", *Oligonucleotides and Analogs A Practical Approach*, 1991, Chapter 1, Ekstein, F., ed., IRL Press, Oxford, 1–24.

Cook, P.D., "Medicinal Chemistry of Antisense Oligonucleotides—future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304.

Efimov, V.A. et al., "New efficient sulfurizing reagents for the preparation of oligodeoxyribonucleotide phosphorothioate analogues", *Nucl. Acids Res.*, 1995, 23, 4029–4033.

Englisch, U. et al., "Chemically Modified Oligonucleotides as Probes and Inhibitors", *Angew. Chem. Int. Ed. Eng.*, 1991, 30, 613–629.

Hamm, M. L. et al., "Incorporation of 2'–Deoxy–2'–mercaptocytidine into Oligonucleotides via Phosphoramidite Chemistry," *J. Org. Chem.*, 1997, 62, 3415– 3420.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

(List continued on next page.)

Primary Examiner—Robert A. Schwartzman
Assistant Examiner—Janet Epps
(74) Attorney, Agent, or Firm—Woodcock Washburn Kurtz Mackiewicz & Norris LLP

(57) ABSTRACT

Synthetic processes are provided wherein mixed backbone oligomeric compounds are prepared having at least one phosphodiester internucleoside linkage in addition to one or more phosphorothioate, phosphoramidate and boranophosphate internucleoside linkages. Novel H-phosphonate intermediates are also disclosed that are useful in the synthetic processes. The synthetic processes use a novel oxidation step to oxidize H-phosphonate internuleoside linkages to phosphodiester internuleoside linkages without degradation of adjacent phosphorothioate, phosphoramidate and boranophosphate internucleoside linkages. Also provided are synthetic intermediates useful in such processes.

40 Claims, No Drawings

OTHER PUBLICATIONS

Iyer, R.P. et al., "The Automated Synthesis of Sulfur–Containing Oligodeoxyribonucleotides Using 3H–1, 2–Benzodithiol–3–one 1,1–Dioxide as a Sulfur– Transfer Reagent", *J. Org. Chem.*, 1990, 55, 4693–4699.

Kamer, P.C.J. et al., "An Efficient Approach Toward the Synthesis of Phosphorothioate Diesters via the Schonberg Reaction", *Tetrahedron Letts.*, 1989, 30, 6757–6760.

Kroschwitz, J.I., "Polynucleotides", *Concise Encyclopedia of Polymer Science and Engineering*, 1990, John Wiley & Sons, New York, 858–859.

Martin, P., "Ein neuer Zugang zu 2'–O–Alkylribonucleosiden und Eigenschaften deren Oligonucleotide", *Helvetica Chemica Acta*, 1995, 78, 486–504 (English abstract included).

Monia et al., "Antitumor activity of a phosphorothioate antisense oligodeoxynucleotide targeted against C–rafkinase", *Nature Medicine*, 1996, 2(6), 668–675.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Polushin, N. N. et al., "Synthesis of Oligonucleotides Containing 2'–Azido–and 2'– Amino–2'–deoxyuridine Using Phosphotriester Chemistry," *Tetrahedron Letts.*, 1996, 37(19), 3227–3230.

Rao, M.V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842.

Ravasio, N. et al., "Selective Hydrogenations Promoted by Copper Catalysts. 1. Chemoselectivity, Regioselectivity, and Stereoselectivity in the Hydrogenation of 3– Substituted Steroids", *J. Org. Chem.*, 1991, 56, 4329–4333.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Secrist, J.A. et al., "Synthesis and Biological Activity of 4'–Thionucleosides", *10th International Roundtable: Nucleosides, Nucleotides and their Biological Applications*, Sep. 16–20 1992, Abstract 21, Park City, Utah, 40.

Sergueev et al., H–Phosphonate Approach for Solid–Phase Synthesis of Oligodeoxyribonucleoside Boranophosphates and Their Characterization, *J. Am. Chem. Soc.*, 1998, 120, 9417–9427.

Stec, W.J. et al., "Bis (O,O–Diisopropoxy Phosphinothioyl) Disulfide—A Highly Efficient Sulfurizing Reagent for Cost–Effective Synthesis of Oligo(Nucleoside Phosphorothioate)s", *Tetrahedron Letts.*, 1993, 34, 5317–5320.

Thomson, J. B. et al., "Synthesis and Properties of Diuridine Phosphate Analogues Containing Thio and Amino Modifications," *J. Org. Chem.*, 1996, 61, 6273–6281.

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008.

Wada et al., "Chemical Synthesis of Oligodeoxyribonucleotides Using N–Unprotected H– Phosphonate Monomers and Carbonium and Phosphonium Condensing Reagents: O–Selective Phosphonylation and Condensation", *J. Am. Chem. Soc.*, 1997, 119, 12710–12721.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

Wu, H. et al., "Inhibition of in vitro transcription by specific double–stranded oligodeoxyribonucleotides", *Gene*, 1990, 89, 203–209.

Xu, Q. et al., "Use of 1,2,4–dithiazolidine (DtsNH) and 3–ethoxy–1,2,4–dithiazoline–5– one (Edith) for synthesis of phosphorothioate–containing oligodeoxyribonucleotides", *Nucl. Acids Res.*, 1996, 24, 1602–1607.

Xu, Q. et al., "Efficient introduction of phosphorothioates into RNA oligonucleotides by 3–ethoxy–1,2, 4–dithiazoline–5–one (Edith)", *Nucl. Acids Res.*, 1996, 24, 3643– 3644.

Ausubel et al. (eds.), *Current Protocols in Molecular Biology*, Current Publications, 1993.

Ekstein, F. (ed.), *Oligonucleotides and Analogues A Practical Approach*, IRL Press, N.Y., 1991.

Greene, T. W. et al., "Protection for the Amino Group," *Protective Groups in Organic Synthesis*, 1991, Chapter 7, John Wiley & Sons, 308–405.

Greene, T. W. et al., "Protection for the Hydroxyl Group Including 1,2– And 1,3– Diols," *Protective Groups in Organic Synthesis*, 1991, Chapter 2, John Wiley & Sons, 10–143.

Sambrook et al. (eds.), *Molecular Cloning, A Laboratory Manual*, Second Edition, Cold Spring Harbor Laboratory Press, 1989.

* cited by examiner

COMPOUNDS, PROCESSES AND INTERMEDIATES FOR SYNTHESIS OF MIXED BACKBONE OLIGOMERIC COMPOUNDS

FIELD OF THE INVENTION

The present invention is directed to methods for oxidizing an H-phosphonate internuleoside linkage in a compound which has at least one 2'-substituent group. This invention further relates to methods for the preparation of mixed backbone oligomeric compounds having internuleoside linkages including phosphodiester, phosphorothioate, phosphoramidate and boranophosphate linkages. The present invention also relates to synthetic intermediates useful in such methods. Also included are mixed backbone oligomeric compounds having phosphodiester and boranophosphate internucleoside linkages or phosphodiester and boranophosphate internucleoside linkages in combination with other internuleoside linkages such as phosphorothioate and phosphoramidate internucleoside linkages. The methods of the present invention include a novel oxidation step that allows oxidation of a region having one or more H-phosphonate internucleoside linkages to phosphodiester internucleoside linkages without degradation of adjacent phosphorothioate, phosphoramidate or boranophosphate internucleoside linkages.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g., fluorescein, biotin, digoxigenin, alkaline phosphatase or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides, their analogs and synthetic processes for their preparation.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is via the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions. Bielinska, et al., *Science*, 1990, 250, 997–1000; and Wu, et al., *Gene*, 1990, 89, 203–209.

In addition to their use as indirect and direct regulators of proteins, oligonucleotides and their analogs also have found use in diagnostic tests. Such diagnostic tests can be performed using biological fluids, tissues, intact cells or isolated cellular components. As with inhibition of gene expression, diagnostic applications utilize the ability of oligonucleotides and their analogs to hybridize with a complementary strand of nucleic acid. Hybridization is the sequence-specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., Sambrook et al., Eds., Cold Spring Harbor Laboratory Press, 1989; and *Current Protocols In Molecular Biology*, Ausubel et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See, also, "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e., increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous processes for coupling nucleosides through phosphorous-containing covalent linkages to produce oligonucleotides of defined sequence. One such method utilizes H-phosphonate monomers to prepare oliogmeric compounds. The standard H-phosphonate method has been used for the synthesis of uniformly modified oligomeric compounds containing phosphodiester, phosphorothioate or phosphoramidate internuleoside linkages. The method has not been effective for the synthesis of mixed backbone oligomers because during the oxidation step previously oxidized regions in an oligomer are degraded. Such degradation has been observed for the oxidation of oligomers having phosphorothioate and or phosphoramidate internucleoside linkages when further H-phosphonate internucleoside linkages are oxidized to phosphodiester linkages.

H-phosphonate methods and techniques are disclosed in numerous publications. See, Mackie and Hogrefe, *Glen Research, H-phosphonate Chemistry*, Glen Research Corp, Va.; Wada et al., *J. Am. Chem. Soc.*, 1997, 119, 12710–12721; and Sergueev et al., *J. Am. Chem. Soc.*, 1998, 120, 9417–9427.

Phosphoramidate oligodeoxynucleotides have been prepared using H-phosphonate chemistry. Dagle et al., *Nucleic Acids Research*, 1991, 19, 1805–1810.

2'-Methoxymethyl oligonucleotides have been prepared using H-phosphonate monomers. Bizdena et al., *Collect. Czech. Chem. Commun.*, 1996, 61, 283–286.

SUMMARY OF THE INVENTION

The present invention provides methods for oxidizing H-phosphonate internucleoside linkages in a compound which bears at least one 2'-substituent group. This oxidation is effected by an oxidizing solution comprising an oxidizing agent, an aprotic solvent, a base and water.

The present invention also provides methods for the preparation of mixed backbone oligomeric compounds of formula:

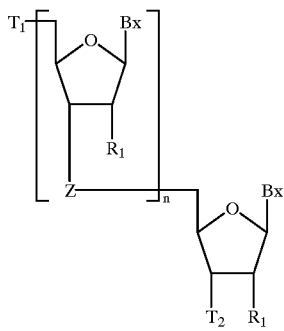

wherein:
each Z is, independently, a phosphodiester, phosphorothioate, phosphoramidate or boranophosphate internuleoside linkage;
each $T_1$ and $T_2$ is, independently, hydroxyl or a protected hydroxyl;
Bx is a heterocyclic base moiety;
each $R_1$ is, independently, H, hydroxyl, a protected hydroxyl, a 2'-substituent group or a protected 2'-substituent group; and
n is an integer greater than 1;
provided that at least one of said Z is a phosphodiester internuleoside linkage and at least another of said Z is a phosphorothioate, phosphoramidate or boranophosphate internuleoside linkage;

comprising the steps of:
(a) providing a compound of formula:

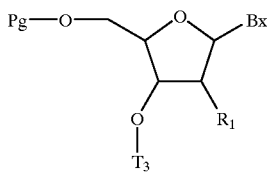

wherein:
Pg is an acid labile hydroxyl protecting group; and
$T_3$ is a base labile hydroxyl protecting group or a covalent attachment to a solid support;

(b) deblocking said acid labile hydroxyl protecting group to form a deblocked hydroxyl group;

(c) treating said deblocked hydroxyl group with a further compound having the formula:

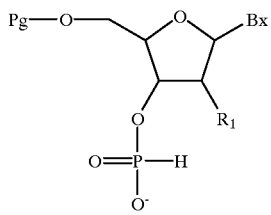

and acondensing reagent in a solvent under conditions of time, temperature and pressure effective to form an extended compound having an added H-phosphonate internucleoside linkage;

(d) optionally treating said extended compound with a capping agent to form a capped compound;

(e) optionally treating said capped compound with a silylating agent to give a silylated compound;

(f) optionally treating said extended compound, said capped compound, or said silylate compound with an oxidizing solution inert to phosphodiester, phosphorothioate, phosphoramidate or boranophosphate internucleoside linkages, thereby oxidizing said H-phosphonate internucleoside linkages to phosphodiester, phosphorothioate, phosphoramidate or boranophosphate internuleoside linkages;

(g) optionally repeating steps (b), (c), (d), (e) and (f) to form a protected oligomeric compound; and (h) treating said protected oligomeric compound with a deblocking solution to form said mixed backbone oligomeric compound.

In a preferred embodiment, the mixed backbone oligomeric compound comprises contiguous regions of phosphodiester and phosphorothioate internuleoside linkages.

In another preferred embodiment, the mixed backbone oligomeric compound comprises contiguous regions of phosphodiester and phosphoramidate internucleoside linkages.

In a further preferred embodiment, the oxidizing solution comprises an oxidizing agent, an aprotic organic solvent, a base and water.

In one embodiment of the present invention the oxidizing solution comprises from about 18% to 45% oxidizing agent.

In a preferred embodiment the oxidizing solution comprises from about 26% to about 40% oxidizing agent. In a more preferred embodiment the oxidizing solution comprises about 33% oxidizing agent.

The present invention also provides compounds of formula:

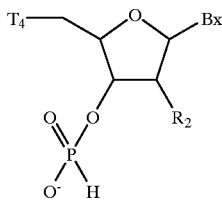

wherein:

$T_4$ is hydroxyl or a protected hydroxyl;

Bx is a heterocyclic base moiety; and $R_2$ has one of formula I or II:

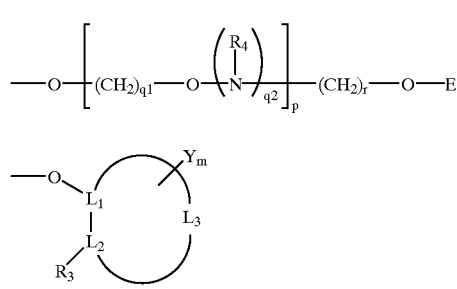

wherein:

E is $C_1$–$C_{10}$ alkyl, $N(R_4)(R_5)$ or $N=C(R_4)(R_5)$;

$R_3$ is OX, SX, or $N(X)_2$;

each $R_4$ and $R_5$ is, independently, H, $C_1$–$C_{10}$ alkyl, a nitrogen protecting group, or $R_4$ and $R_5$, together, are a nitrogen protecting group, or $R_4$ and $R_5$ are joined in a ring structure that can include at least one additional heteroatom selected from a group consisting of nitrogen and oxygen;

each X is, independently, H, $C_1$–$C_8$ alkyl, $C_1$–$C_8$ haloalkyl, $C(=NH)N(H)Z$, $C(=O)N(H)Z$ or $OC(=O)N(H)Z$;

Z is H or $C_1$–$C_8$ alkyl;

$L_1$, $L_2$ and $L_3$ comprise a ring system having from about 4 to about 7 carbon atoms or having from about 3 to about 6 carbon atoms and at least 1 heteroatom, said heteroatom being selected from a group consisting of oxygen, nitrogen and sulfur, said ring system being aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_4)(R_5)$ $OR_4$, halo, $SR_4$ or CN;

each $q_1$ is, independently, an integer from 2 to 10;

each $q_2$ is, independently, 0 or 1;

p is an integer from 1 to 10; and r is an integer from 1 to 10, provided that when p is 0, r is an integer greater than 1.

In a preferred embodiment $R_2$ is a 2'-substituent group. In another preferred embodiment the 2'-substituent group is —O—$CH_2CH_2$—O—$CH_3$, —O—$CH_2CH_2$—O—$N(R_6)(R_7)$ or —O—$CH_2CH_2$—O—$CH_2CH_2$—$N(R_6)(R_7)$, wherein each of $R_6$ and $R_7$ is, independently, H or $C_1$–$C_{10}$ alkyl. In a further preferred embodiment each $R_6$ and $R_7$ is —$CH_3$.

The present invention also provides chimeric oligomeric compounds having the formula:

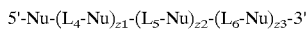

wherein:

each $L_4$, $L_5$, and $L_6$ is, independently, an internucleoside linkage selected from phosphodiester, phosphorothioate, phosphoramidate or boranophosphate, with the provision that $L_4$ and $L_6$ are different from $L_5$ and that one of $L_4$, $L_5$ and $L_6$ are other than phosphodiester and phosphorothioate;

each $z_1$, $z_2$, and $Z_3$ is, independently, an integer greater than 1;

each Nu is a nucleoside having the formula:

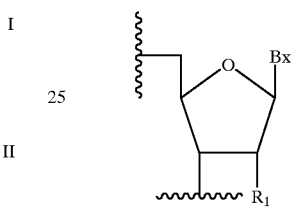

wherein:

Bx is a heterocyclic base moiety;

each $R_1$ is, independently, H, hydroxyl, a protected hydroxyl, a 2'-substituent group or a protected 2'-substituent group; and said 5'- and said -3' ends of said chimeric oligomeric compound are, independently, hydroxyl, a protected hydroxyl, a linkage to a solid support, an activated phosphate group, an activated phosphite group, a reactive group for forming an internuleotide linkage, a nucleotide, a nucleoside, or an oligonucleotide.

In one embodiment, each $L_4$ and $L_6$ is a phosphoramidate internucleotide linkage and each $L_5$ is a phosphorothioate internuleoside linkage.

In another embodiment, each $L_4$ and $L_6$ is a phosphoramidate internucleotide linkage and each $L_5$ is a phosphodiester internucleoside linkage.

In yet another embodiment, each $L_4$ and $L_6$ is a boranophsphate internucleotide linkage and each $L_5$ is a phosphodiester internucleoside linkage.

In a further embodiment, each $L_4$, $L_5$ and $L_6$ is phosphoramidate, phosphorothioate or phosphodiester.

It is preferred that each $R_1$ be, independently, —O—$CH_2CH_2$—O—$CH_3$, —O—$CH_2CH_2$—O—$N(R_6)(R_7)$ or —O—$CH_2CH_2$—O—$CH_2CH_2$—$N(R_6)(R_7)$. It is also preferred that each of $R_6$ and $R_7$ be, independently, H or $C_1$–$C_{10}$ alkyl.

It is further preferred that each $R_6$ and $R_7$ be —$CH_3$.

DETAILED DESCRIPTION OF PREFERRED EMBODIMENTS

The present invention provides compounds and methods for the preparation of mixed backbone oligomeric, or chimeric, compounds having phosphodiester internucleoside linkages in addition to phosphorothioate and/or phosphoramidate internucleoside linkages. The methods also include incorporation of boranophosphate internucleoside linkages into oligomeric compounds of the invention. The methods utilize H-phosphonate intermediates that are coupled together forming contiguous regions of one or more H-phosphonate internucleoside linkages. Each contiguous region is subsequently oxidized to phosphodiester, phosphorothioate, phosphoramidate or boranophosphate internucleoside linkages prior to further elongation. Mixed backbone oligomeric compounds are prepared in this manner by oxidizing adjacent regions with different reagents. Oligomeric compounds of the invention are prepared using novel oxidation steps that oxidize a region of one or more H-phosphonate internucleoside linkages without degrading existing linkages that have been previously oxidized.

The H-phosphonate method of oligomer synthesis has been used for the preparation of oligonucleotides and their analogs having a variety of internucleotide linkages. These internucleotide linkages have included phosphorothioate, phosphoramidate, methyl phosphate, methylphosphonate, alkylphosphonate, S-aryl phosphorothioate, acylphosphonate, phosphorofluoridate, phosphorodithioate, selenophosphate, (hydroxymethyl)phosphonate and boranophosphate.

As used herein, the term "chimeric oligomeric compound" or "mixed backbone oligomeric compound" refers to oligomeric compounds comprising nucleoside monomer subunits and containing at least two different internuleoside linkages. The mixed backbone oligomeric compounds of the present invention may contain a plurality of nucleoside monomer subunits that are joined together by more than one type of internucleoside linkages. At least one internucleoside linkage is a phosphodiester linkage and at least one other linkage is a phosphorothioate, a phosphoramidate or a boranophosphate internuleoside linkage. Thus the term "oligomeric compound" includes oligonucleosides, oligonucleotides, their analogs, and synthetic oligonucleotides.

In some preferred embodiments, a first monomer attached to a solid support is elongated using H-phosphonate monomers. The methods of the present invention have been used with automated DNA synthesizers to synthesize mixed backbone oligomeric compounds of desired length and sequence. Some oligomeric compounds have been synthesized having only phosphodiester and phosphorothioate internucleoside linkages. Other oligomeric compounds have been synthesized having phosphodiester, phosphorothioate and phosphoramidate internucleoside linkages. Example 14 illustrates the synthesis of a boranophosphate mixed backbone oligomeric compound. Table I illustrates selected oligomeric compounds that were synthesized using methods and intermediates of the present invention.

In preferred embodiments, the methods of the present invention are employed for use in iterative solid phase oligonucleotide synthetic regimes. Representative solid phase techniques are those typically employed for DNA and RNA synthesis utilizing standard H-phosphonate chemistry. The H-phosphonate method of oligonucleotide synthesis is disclosed in U.S. Pat. No. 5,149,798, issued Sep. 22, 1992, and U.S. Pat. No. 5,548,076, issued Aug. 20, 1996. The entire disclosure of each is incorporated herein by reference. A preferred synthetic solid phase synthesis utilizes H-phosphonates as activated phosphate compounds. In this technique, an H-phosphonate monomer is reacted with a free hydroxyl on the growing oligomer chain to produce an intermediate phosphite compound, which is subsequently oxidized to the $P^V$ state. This technique is commonly used for the synthesis of several types of linkages including phosphodiester, phosphorothioate, and phosphoramidate linkages. Oxidation of H-phosphonate linkages to phosphodiester linkages using standard H-phosphonate chemistry results in the degradation of phosphorothioate and phosphoramidate linkages when present in a growing oligomeric compound. This degradation of adjacent linkages within an oligomeric compound has been a limitation to the use of standard H-phosphonate chemistry with mixed backbone syntheses.

Typically, the first step in such a process is attachment of a monomer or higher order subunit containing a protected 5'-hydroxyl to a solid support, usually through a linker, using standard methods and procedures known in the art. See, e.g., *Oligonucleotides And Analogues A Practical Approach*, Ekstein, F. Ed., IRL Press, N.Y., 1991, hereby incorporated by reference in its entirety. The support-bound monomer or higher order first synthon is then treated to remove the 5'-protecting group. Typically, this is accomplished by treatment with acid. The solid support bound monomer is then reacted with a second monomer or higher order synthon having a reactive group for forming an internuleoside linkage. In preferred embodiments the coupling reaction is performed under anhydrous conditions in the presence of a condensing reagent.

After the addition of each monomer or higher order synthon, a capping step is performed to cap unreacted hydroxyl groups. It is generally preferable to perform a capping step either prior to or after oxidation or sulfurization of the internuleoside linkage. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

As used herein an "oxidizing solution" comprises a mixture of reagents effective to oxidize an H-phosphonate internuleoside linkage or silylated derivative thereof to a phosphodiester, phosphorothioate, phosphoramidate or boranophosphate internuleoside linkage. Such oxidation can be performed on a region of an oligomeric compound without causing degradation of other previously oxidized portions of the same oligomeric compound. Oxidation of each type of internuleoside linkage is illustrated in the examples below. Oxidation of the internuleoside linkage can be performed iteratively after each coupling step, or can be performed after a desired number or sequence of monomers have been coupled. This allows for the preparation of gapmer-type oligomeric compounds having one or more regions of one type of linkage with one or more other regions having another type of linkage. A representative example of a gapmer is an oligomeric compound having a phosphorothioate region at the 3' and 5' ends with a phosphodiester region located internally.

Treatment of the growing oligomeric compound with an acid removes the 5'-hydroxyl protecting group enabling another synthetic iteration. The growing oligomeric compound is extended with subsequent oxidation at selected stages with selected oxidation agents until an oligomeric compound of desired length is produced.

The completed oligomer is then cleaved from the solid support. The cleavage step can precede or follow deprotection of protected functional groups. The term "deblocking solution" as used herein is meant to encompass solutions routinely used for the deblocking of oligomeric compounds prepared either by solution or solid phase techniques. A common solution used for deblocking of oligomers synthesized on solid support is aqueous ammonia.

As used herein "heterocyclic base moiety" is intended to include nucleobases. Nucleobases useful in the compounds and methods described herein include but are not limited to adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally- and non-naturally-occurring nucleobases include those disclosed in U.S. Patent No. 3,687,808 (Merigan et al.); in Sanghvi, in *Antisense Research and Application*, Chapter 15, S. T. Crooke and B. Lebleu, Eds., CRC Press, 1993; in Englisch et al., *Angewandte Chemie*, International Edition, 1991, 30, 613–722 (particularly, pages 622 and 623); in the *Concise Encyclopedia of Polymer Science and Engineering*, J. I. Kroschwitz, Ed., John Wiley & Sons, 1990, pages 858–859; and in Cook, *Anti-Cancer Drug Design*, 1991, 6, 585–607, each of which is hereby incorporated by reference in its entirety. The term "nucleosidic base moiety" is further intended to include heterocyclic compounds that can serve as nucleosidic bases, including certain 'universal bases' that are not nucleosidic bases in the most classical sense but serve as nucleosidic bases. Especially mentioned as a universal base is 3-nitropyrrole.

As used herein, the term "2'-substituent group" includes 2'-sugar modifications. 2'-Sugar modifications of the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and PEG-containing groups, such as crown ethers and those which are disclosed by Ouchi et al., *Drug Design and Discovery* 1992, 9, 93; Ravasio et al., *J. Org. Chem.* 1991, 56, 4329; and Delgardo et. al., *Critical Reviews in Therapeutic Drug Carrier Systems* 1992, 9, 249, each of which is hereby incorporated by reference in its entirety. Further sugar modifications are disclosed in Cook, *Anti-Cancer Drug Design*, 1991, 6, 585–607. Fluoro, O-alkyl, O-alkylamino, O-alkyl imidazole, O-alkylaminoalkyl, and alkyl amino substitutions are described in U.S. patent application Ser. No. 08/398,901, filed Mar. 6, 1995, entitled "Oligomeric Compounds having Pyrimidine Nucleotide(s) with 2' and 5' Substitutions," hereby incorporated by reference in its entirety.

Additional 2'-sugar modifications of use in the present invention include 2'-SR and 2'-NR$_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. Incorporation of 2'-SR monomer synthons is disclosed by Hamm et al., *J. Org. Chem.*, 1997, 62, 3415–3420. 2'-NR$_2$ nucleosides are disclosed by Goettingen, *J. Org. Chem.*, 1996, 61, 6273–6281; and Polushin et al., *Tetrahedron Lett.*, 1996, 37, 3227–3230. Some representative 2'-sugar modifications amenable to the present invention include those having one of formula I or II:

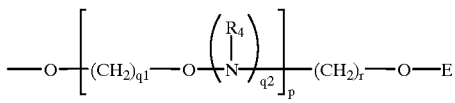

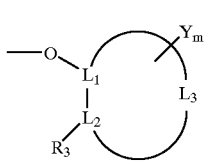

wherein:

E is $C_1$–$C_{10}$ alkyl, $N(R_4)(R_5)$ or $N=C(R_4)(R_5)$;

each $R_4$ and $R_5$ is, independently, H, $C_1$–$C_{10}$ alkyl, a nitrogen protecting group, or $R_4$ and $R_5$, together, are a nitrogen protecting group, or $R_4$ and $R_5$ are joined in a ring structure that can include at least one additional heteroatom selected from a group consisting of nitrogen and oxygen;

$R_3$ is OX, SX, or $N(X)_2$;

each X is, independently, H, $C_1$–$C_8$ alkyl, $C_1$–$C_8$ haloalkyl, $C(=NH)N(H)Z$, $C(=O)N(H)Z$ or $OC(=O)N(H)Z$;

Z is H or $C_1$–$C_8$ alkyl;

$L_1$, $L_2$ and $L_3$ comprise a ring system having from about 4 to about 7 carbon atoms, or having from about 3 to about 6 carbon atoms and at least one heteroatom, said heteroatom being selected from a group consisting of oxygen, nitrogen and sulfur, said ring system being aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_4)(R_5)$ $OR_4$, halo, $SR_4$ or CN;

each $q_1$ is, independently, from 2 to 10;

each $q_2$ is, 0 or 1;

p is from 1 to 10; and r is from 1 to 10, provided that when p is 0, r is greater than 1.

Representative 2'-sugar substituents of formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic 2'-sugar substituents of formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Sugars wherein the ring oxygen atom is replaced by other atoms are also amenable to the present invention. Representative substitutions for the ring oxygen include S, $CH_2$, CHF, and $CF_2$. See, e.g., Secrist et al., *Abstract 21, Program & Abstracts, Tenth International Roundtable, Nucleosides, Nucleotides and their Biological Applications*, Park City, Utah, Sep. 16–20, 1992, hereby incorporated by reference in its entirety.

As used herein, the term "alkyl" includes, but is not limited to, straight chain, branched chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. As used herein, the term "lower alkyl" is intended to mean alkyl having 6 or fewer carbons.

As used herein, the term "aralkyl" denotes alkyl groups which bear aryl groups, for example, benzyl groups. The term "alkaryl" denotes aryl groups which bear alkyl groups, for example, methylphenyl groups. As used herein the term "aryl" denotes aromatic cyclic groups including but not limited to phenyl, naphthyl, anthracyl, phenanthryl, and pyrenyl.

As used herein, the term "alkanoyl" has its accustomed meaning as a group of formula —C(=O)-alkyl. A preferred alkanoyl group is the acetyl group.

In general, the term "hetero" denotes an atom other than carbon, preferably but not exclusively nitrogen, oxygen or sulfur. Accordingly, the term "heterocycloalkyl" denotes an alkyl ring system having one or more heteroatoms, i.e., non-carbon atoms. Preferred heterocycloalkyl groups include, for example, morpholino groups. As used herein, the term "heterocycloalkenyl" denotes a ring system having one or more double bonds and one or more heteroatoms. Preferred heterocycloalkenyl groups include, for example, pyrrolidino groups.

In a preferred embodiment of the present invention, oligomer synthesis is performed on an automated synthesizer utilizing a solid support. Solid supports are substrates which are capable of serving as the solid phase in solid phase synthetic methodologies, such as those described in U.S. Pat. Nos. 4,415,732; 4,458,066; 4,500,707; 4,668,777; 4,973,679; 5,132,418; 4,725,677 and Re. 34,069. Linkers are known in the art as short molecules which serve to connect a solid support to functional groups, e.g., hydroxyl groups, of initial synthon molecules in solid phase synthetic techniques. Suitable linkers are disclosed in, for example, *Oligonucleotides And Analogues A Practical Approach*, Ecstein, F., Ed., IRL Press, N.Y., 1991, Chapter 1, pages 1–23.

Solid supports according to the invention include those generally known in the art to be suitable for use in solid phase methodologies including, for example, controlled pore glass (CPG), oxalyl-controlled pore glass (see, e.g., Alul et al., *Nucleic Acids Research* 1991, 19, 1527, hereby incorporated by reference in its entirety), TentaGel Support; an aminopolyethyleneglycol derivatized support (see, e.g., Wright et al., *Tetrahedron Letters* 1993, 34, 3373, hereby incorporated by reference in its entirety) and Poros; a copolymer of polystyrene/divinylbenzene.

In some embodiments of the invention, each of $T_1$ and $T_2$ is, independently, a protected hydroxyl group, and $T_3$ is a hydroxyl protecting group. A wide variety of hydroxyl protecting groups can be employed in the methods of the invention. Preferably, the protecting group is stable under either acidic or basic conditions. This enables removal of a base-stable protecting group under acidic conditions, and removal of an acid-stable protecting group under basic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage et al., *Tetrahedron* 1992, 48, 2223–231 1, and also in Greene and Wuts, *Protective Groups in Organic Synthesis*, Chapter 2, 2d ed, John Wiley & Sons, New York, 1991, each of which is hereby incorporated by reference in its entirety. Preferred protecting groups include dimethoxytrityl (DMT), monomethoxytrityl (MMT), 9-phenylxanthen-9-yl (Pixyl) and 9-(p-methoxyphenyl)xanthen-9-yl (Mox).

In some preferred embodiments of the invention amino groups are appended to alkyl or other groups such as, for example, 2'-alkoxy groups. Such amino groups are also commonly present in naturally-occurring and non-naturally-occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected," when used in connection with a molecular moiety such as "nucleobase," indicates that the molecular moiety contains one or more functionalities protected by protecting groups.

There are currently many useful condensing reagents known to the art skilled that are amenable to the H-phosphonate method of oligonucleotide synthesis. Wada et al., *J. Am. Chem. Soc.*, 1997, 119, 12710–12721. Useful condensing reagents include, but are not limited to, acid chlorides, chlorophosphates, carbonates, carbonium type compounds and phosphonium type compounds. In a preferred embodiment the condensing reagent is selected from a group consisting of pivaloyl chloride, adamantyl chloride, 2,4,6-triisopropyl-benzenesulfonyl chloride, 2-chloro-5,5-dimethyl-2-oxo-1,3,2-dioxaphosphinane, diphenyl phosphorochloridate, bis(2-oxo-3-oxazolidinyl)phosphinic chloride, bis(pentafluorophenyl)carbonate, 2-(1H-benzotriazole-1-yl)-1,1,3,3-tetramethyluronium hexafluorophosphate, O-(azabenzotriazol-1-yl)-1,1,3,3-tetramethyl uronium hexafluorophosphate, 6-(trifluoromethyl)benzotriazol-1-yl-oxy-tris-pyrrolidino-phosphonium hexafluorophosphate, bromo-tris-pyrrolidino-phosphonium hexafluorophosphate, benzotriazole-1-yl-oxy-tris-pyrrolidino-phosphonium hexafluorophosphate and 2-(benzotriazol-1-yloxy)-1,3-dimethyl-2-pyrrolidin-1-yl-1,3,2-diazaphospholidinium hexafluorophosphate.

Sulfurizing agents used during oxidation to form phosphorothioate and phosphorodithioate linkages, when they are the only linkages present, include Beaucage reagent (Iyer et.al., *J. Chem. Soc.*, 1990, 112, 1253–1254; and Iyer et.al., *J. Org. Chem.*, 1990, 55, 4693–4699); tetraethylthiuram disulfide (Vu and Hirschbein, *Tetrahedron Lett.*, 1991, 32, 3005–3008); dibenzoyl tetrasulfide (Rao, et.al., *Tetrahedron Lett.*, 1992, 33, 4839–4842); di(phenylacetyl)disulfide (Kamer, *Tetrahedron Lett.*, 1989, 30, 6757–6760); Bis(O,O-diisopropoxy phosphinothioyl)disulfides (Stec et al., *Tetrahedron Lett.*, 1993, 34, 5317–5320); 3-ethoxy-1,2,4-dithiazoline-5-one (*Nucleic Acids Research*, 1996 24, 1602–1607; and *Nucleic Acids Research*, 1996 24, 3643–3644); bis(p-chlorobenzenesulfonyl)-disulfide (*Nucleic Acids Research*, 1995 23, 4029–4033); sulfur, and sulfur in combination with ligands such as triaryl, trialkyl, triaralkyl, or trialkaryl phosphines. Each of the foregoing references is hereby incorporated by reference in its entirety.

Useful oxidizing agents used to form the phosphodiester or phosphorothioate linkages, when they are the only linkages present, include iodine/tetrahydrofuran/water/pyridine, hydrogen peroxide/water, tert-butyl hydro peroxide or any peracid like m-chloroperbenzoic acid. In the case of oxidation using a sulfur species, the reaction is performed under anhydrous conditions with the exclusion of air, in particular oxygen, whereas in the case of oxidation the reaction can be performed under aqueous conditions.

The oxidation of H-phosphonate internucleoside linkages, without simultaneous degradation of existing, previously oxidized linkages, is performed using a novel oxidizing solution. The oxidizing solution comprises particular compounds/reagents dependent upon what oxidized linkages are being prepared from the H-phosphonate linkages. In general, the oxidation solution comprises an oxidizing agent, an aprotic organic solvent, and a base.

Bases are present in the oxidizing solution to assist in the oxidation process. Selected bases have a pka ranging from about 9 to about 12, which is believed to be the optimum range for deprotonation of H-phosphonate or water without causing cleavage of the backbone of the oligomeric compound. While not wanting to be bound by theory, it is believed that bases within this pKa range, and present in the oxidation solution in a concentration of from about 0.01 to about 0.8 M, are necessary for oxidation of H-phosphonate linkages without simultaneous degradation of existing oxidized linkages. A more preferred range for the concentration of the base is from about 0.05 to about 0.2 M in the oxidation solution. Representative bases that are useful in the present invention include 4-(dimethylamino)pyridine (DMAP), triethylamine (TEA) and N,N-diisopropylethylamine (DIEA).

Many aprotic organic solvents known to those skilled in the art are amenable to the present invention. Some representative aprotic organic solvents include pyridine, acetonitrile and dimethylformamide.

The choice of oxidizing agent is dependent on the particular internucleoside linkage that is desired for the region of H-phosphonate internuleoside linkages that is being oxidized. Representative oxidizing agents useful for the preparation of phosphodiester internuleoside linkages include carbon tetrachloride, carbon tetrabromide, N-chlorosuccinimide and N-bromosuccinimide. In addition to an oxidizing agent, water is a necessary component of the oxidizing solution for preparing phosphodiester linkages.

Phosphorothioate internucleoside linkages are prepared using an oxidizing agent that oxidizes phosphorus by addition of sulfur rather than oxygen. Elemental sulfur has been used to sulfurize H-phosphonate to form phosphorothioate internucleoside linkages as illustrated in the examples below. The use of elemental sulfur in the oxidizing solution affords the desired phosphorothioate internucleoside linkages while leaving unaffected any preexisting oxidized linkages in the same oligomeric compound.

The selective oxidation of H-phosphonate internucleoside linkages to phosphodiester, phosphorothioate, phosphoramidate and boranophosphate internucleoside linkages in a mixed backbone oligomeric compound is dependent on the oxidizing solution. The oxidizing solution must not affect preexisting linkages in the oligomeric compound that is undergoing oxidation. The oxidizing solution is a mixture of an oxidizing agent, an aprotic solvent and a base. For phosphodiester linkages water is also a component of the oxidizing solution. The concentration of reagents in the oxidizing solution for a given oxidation can vary. Optimal concentration of reagents can be discerned by the art-skilled without undue experimentation.

The composition and concentration of reagents in the oxidizing solution used to oxidize an H-phosphonate linkages in a mixed backbone oligomeric compound is variable dependent on whether the desired oxidized linkage is phosphodiester, phosphorothioate or phosphoramidate. In the case of boranophosphate internucleoside linkages, a silylation step is also involved. The two main components are the base and the oxidizing agent. For phosphodiester and phosphorothioate internucleoside linkages, an aprotic organic solvent is also used. Water is also used in the oxidizing solution when phosphodiester linkages are prepared.

The oxidizing solution used for preparing phosphodiester internucleoside linkages in a mixed backbone oligomeric compound of the invention generally has from about 18% to about 45% oxidizing agent, from about 2% to about 15% water, from about 40% to about 80% aprotic organic solvent, and from about 0.01 M to about 0.8 M base dissolved in the aprotic organic solvent. A more preferred range of concentrations is from about 26% to about 40% oxidizing agent, from about 4% to about 10% water, from about 50% to about 70% aprotic organic solvent, and from about 0.04 M to about 0.4 M base dissolved in the aprotic organic solvent. Even more preferred is about 33% oxidizing agent, about 7% water, about 60% aprotic organic solvent, and from about 0.05 M to about 0.2 M base dissolved in the aprotic organic solvent.

The oxidizing solution used for preparing phosphorothioate internuleoside linkages in a mixed backbone oligomeric compound of the invention generally has from about 1% to about 15% oxidizing agent, about 40% to about 60% solvent that will solubilize the oxidizing agent, from about 40% to about 60% aprotic organic solvent, and from about 0.01 M to about 0.8 M base dissolved in the aprotic organic solvent. A more preferred range of concentrations is from about 1% to about 10% oxidizing agent, about 40% to about 60% solvent that will solubilize the oxidizing agent, from about 40% to about 60% aprotic organic solvent, and from about 0.02 M to about 0.5 M base dissolved in the aprotic organic solvent. Even more preferred is about 3% to about 8% oxidizing agent, about 40% to about 60% solvent that will solubilize the oxidizing agent, from about 40% to about 60% aprotic organic solvent, and from about 0.04 M to about 0.1 M base dissolved in the aprotic organic solvent.

The oxidizing solution used for preparing phosphoramidate internuleoside linkages in a mixed backbone oligomeric compound of the invention generally has a primary or secondary amine in combination with an oxidizing agent. An oxidizing agent that acts as a solvent for the primary or secondary amine is preferable. A preferred oxidizing agent is carbon tetrachloride. The oxidizing solution has from about 1% to about 15% of the primary or secondary amine, and from about 85% to about 99% oxidizing agent. A preferred concentration is about 1% to about 10% of the primary or secondary amine, and from about 90% to about 99% oxidizing agent. A more preferred concentration of primary or secondary amine is about 2% to about 5% by volume in the oxidizing solution.

The conversion of H-phosphonate internuleoside linkages to the boranophosphate (O=P—BH$_3$) internuleoside linkages requires an additional silylation step prior to the oxidation step. Sergueev et al., *J. Am. Chem. Soc.*, 1998, 120, 9417–9427. A number of silylating agents have been shown to be effective in the silylation step including chlorotrimethyl-silane, N,O-bis-(trimethylsilyl)acetamide, heptamethyldisilazane and N,O-bis-(trimethylsilyl) trifluoroacetamide. The silylation step is followed by oxidation with borane-N,N-diisopropylethylamine (BH$_3$× DIEA, 0.1 mmol to 1 mmol), borane-2-chloro-pyridine or borane-aniline.

In one aspect of the present invention, the compounds of the invention are used to modulate RNA or DNA encoding a protein whose formation or activity is to be modulated. The targeting portion of the composition to be employed is, thus, selected to be complementary to the preselected portion of DNA or RNA. That is, the targeting portion of the composition is hybridizable to the preselected portion of DNA.

The methods of the present invention can be used to prepare oligomeric compounds that are used in diagnostics, therapeutics, and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid encoding the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLE 1

General Procedure

Solid phase synthesis of mixed backbone oligomeric compounds using 2'-O-methoxyethyl-3'-H-phosphonate monomers Reagents Selected solvents and reagents were purchased from Aldrich Chemical Company and J. T. Baker Company. Phosphorus trichloride, pivaloyl chloride, N-methylmorpholine, triethylamine, diazabicyclo[5.4.0]undec-7-ene and 1,2,4-triazole were purchased from Fluka. Pivaloyl chloride was distilled prior to its use for solid phase synthesis. The 5'-O-DMT-2'-O-methoxyethyl mononucleosides were prepared as per known literature methods. Martin, *Helv. Chim. Acta*, 1995, 78, 486–504; Altmann et al., *Chimia*, 1996, 50, 168–176; Altmann et al., *Biochem. Soc. Trans.*, 1996, 24, 630–637; and Altmann et al., *Nucleosides Nucleotides*, 1997, 16, 917–926. Unmodified H-phosphonate mononucleotides, and the capping reagent isopropylphosphite were purchased from Glen Research.

Solid Phase Synthesis

Solid phase synthesis was carried out using an Applied Biosystems (Perkin Elmer Corporation) DNA/RNA synthesizer 380B and controlled pore glass (5'-O-DMT-2'-MOE mononucleoside-3'-succinate: R. I. Chemical, Costa Mesa, Calif.) or primer support (5'-O-DMT-2'-MOE mononucleoside-3'-succinate: Pharmacia) as the solid supports. The H-phosphonate method of oligonucleotide synthesis is disclosed in U.S. Pat. No. 5,149,798, issued Sep. 22, 1992, and U.S. Pat. No. 5,548,076, issued Aug. 20, 1996. The entire disclosure of each is incorporated herein by reference.

The synthesis cycle was based on the H-phosphonate method and included three reaction steps and several washing steps as follows:

(i) Deblocking (DMT cleavage) with dichloroacetic acid (3%) in dichloromethane;
   Washing with acetonitrile; and
   Washing with acetonitrile/pyridine (1:1).

(ii) Coupling of the 5'-O-DMT-H-phosphonate mononucleotide with the deblocked nucleotide using 10 equivalents of mononucleotide and 40 equivalents of pivaloylchloride (0.2 M) in acetonitrile/pyridine (1:1); and
   Washing with acetonitrile/pyridine (1:1).

(iii) Capping (optional) of unreacted 5'-hydroxy functions using 16 equivalents of isopropylphosphite and 64 equivalents of pivaloylchloride (0.2 M) in acetonitrile/pyridine (1:1);
   Washing with acetonitrile/pyridine (1:1); and
   Washing with acetonitrile.

Cleavage from the solid support and deprotection of the oligonucleotides was carried out using aqueous ammonia (25–28%) for 1.5 hours on a column followed by heating at 55° C. for 6 hours.

Oxidation Procedures

Phosphodiester internucleoside linkages in mixed backbone oligomeric compounds:

Mixed backbone oligomeric compounds were prepared having phosphodiester linkages as well as phosphorothioate and/or phosphoramidate linkages. The oxidation of H-phosphonate internuleoside linkages to phosphodiester linkages was performed with reagents inert to existing phosphorothioate and phosphoramidate linkages. One oxidation solution that was effective to convert H-phosphonate to phosphodiester and that was inert to existing phosphorothioate and phosphoramidate internucleoside linkages was triethylamine (0.1 M) or 4-(dimethylamino)pyridine (DMAP, 0.1 M) in pyridine/carbon tetrachloride/water (9:5:1). The reaction time for this oxidation step was 60 to 120 minutes.

The standard oxidation procedures used for H-phosphonate synthesis are based on various formulations containing iodine as the oxidation reagent. However, when preparing mixed backbone oligomeric compounds having in addition to phosphodiester one or both of phosphorothioate and phosphoramidate internucleoside linkages present, the use of iodine significantly affects product homogeneity leading to partial degradation of phosphorothioate linkages or replacement of phosphoramidate linkages with phosphodiester linkages.

The mild oxidation procedures shown in the reaction scheme below illustrate the facile preparation of mixed backbone oligomeric compounds. The oxidation of one or more consecutive internuleoside linkages from H-phosphonate to phosphodiester is performed under reaction conditions which are inert to phosphorothioate or phosphoramidate internuleoside linkages.

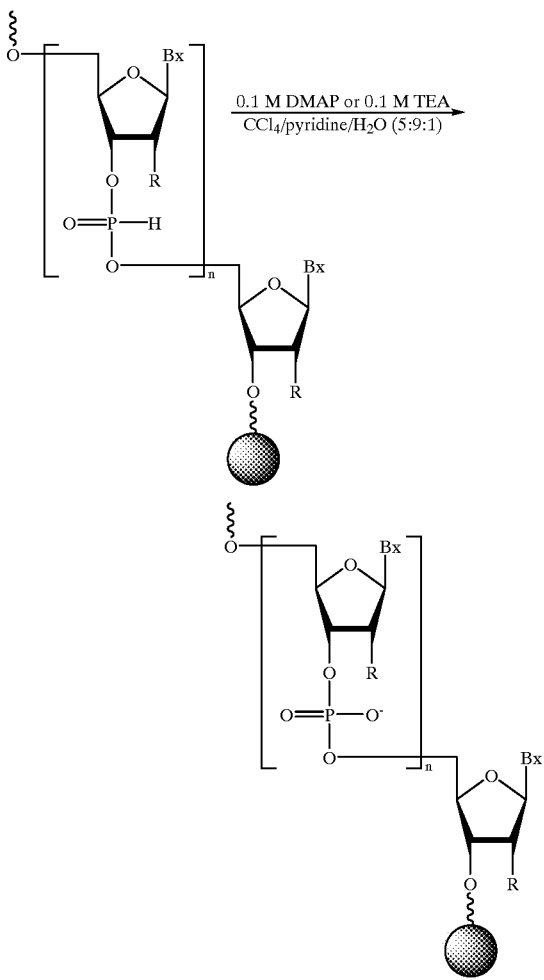

Phosphorothioate internucleoside linkages: Phosphorothioate linkages were prepared via oxidation of H-phosphonate linkages using 5% elemental sulfur in carbon disulfide/pyridine/triethylamine (10:10:1). Prior to sulfurization, the solid support was thoroughly washed with acetonitrile and dried under vacuum. The reaction time was 60 to 120 minutes.

For oligomeric compounds containing phosphorothioate and phosphoramidate linkages the oxidation is performed using 5% elemental sulfur and DMAP (0.1 M) or triethylamine (0.1 M) in carbon disulfide/pyridine(1:1). Prior to sulfurization, the solid support is thoroughly washed with acetonitrile and dried under vacuum. The reaction time is 60–120 min.

Phosphoramidate internucleoside linkages: Oligomeric compounds containing phosphoramidate linkages were prepared via oxidation of the corresponding H-phosphonate oligomer blocks on the solid support using a mixture of a primary or secondary amine in carbon tetrachloride (10%:90%, v/v). Prior to oxidation, the solid support was thoroughly washed with acetonitrile and dried under vacuum. The reaction time was 60 to 120 minutes.

Boranophosphate internucleoside linkages: Oligomeric compounds containing boranophosphate linkages are prepared by treatment of H-phosphonate internuleoside linkages with N,O-bis(trimethylsilyl)trifluoroacetamide (0.3 M) in dry tetrahydrofuran for 20 to 30 minutes, washing with tetrahydrofuran and then treating with borane-N,N-diisopropylethylamine ($BH_3$:DIEA, 0.1 mmol:1 mmol), borane-2-chloropyridine or borane-aniline. Prior to oxidation, the solid support is thoroughly washed with acetonitrile and dried under vacuum. The reaction time is 60 to 240 minutes.

EXAMPLE 2

5'-O-DMT-2'-MOE-thymidine-3'-H-phosphonate

To a stirred solution of 1,2,4-triazole (7.75 g, 0.112 mole) and N-methylmorpholine (33.4 g, 0.33 mole) in dichloromethane (330 mL) was added phosphorus trichloride (4.53 g, 0.033 mole). After stirring for 30 minutes at room temperature the mixture was cooled down to ° C. Subsequently 5'-O-DMT-2'-MOE-thymidine (4 g, 6.6 mmole) in dichloromethane (100 mL) was added dropwise over a period of 20 minutes. After stirring for another 20 min, the mixture was allowed to warm up to room temperature and poured into aqueous triethylammonium bicarbonate buffer (350 mL, pH 8.5) with stirring. The mixture was transferred to a separatory funnel and separated. The aqueous phase was extracted once with dichloromethane (300 mL) and the combined organic phases were washed with another triethylammonium bicarbonate buffer (350 mL). After drying the organic phase over sodium sulfate, the solvent was evaporated and the crude product was dried under vacuum. The crude product was purified by silica gel column chromatography using a step gradient of 0.5% triethylamine in dichloromethane to 0.5% triethylamine in dichloromethane/methanol (9:1). The combined product fractions were evaporated to a foam and evaporated twice with acetonitrile to remove excess triethylamine. Subsequently the purified product was dissolved in dichloromethane (300 mL), washed twice each with 0.2 M diazabicyclo[5.4.0]undec-7-ene bicarbonate buffer (350 mL, pH 8.7), dried over sodium sulfate and evaporated to a foam. Prior to its use for solid phase synthesis the product was dried under high vacuum to give 4.62 g (85%) of the title compound.

$^{31}$P-NMR ($CDCl_3$, using 2% $H_3PO_4$ as an external standard) 4.22 ppm.

EXAMPLE 3

5'-O-DMT-2'-MOE-N-6-benzoyladenosine-3'-H-phosphonate

To a stirred solution of 8.03 g (0.116 mole) 1,2,4-triazole and 34.6 g (0.342 mole) N-methylmorpholine in 340 mL dichloromethane 4.7 g (0.0342 mole) of phosphorus trichloride were added. The mixture was stirred for 30 min at room temperature and cooled down to 0° C. Subsequently, 5'-O-DMT-2'-MOE-N-6-benzoyladenosine (5 g, 6.84 mmole) in dichloromethane (100 mL) was added dropwise over a period of 20 minutes. After stirring for another 20 minutes, the mixture was allowed to warm up to room temperature and poured into aqueous triethylammonium bicarbonate buffer (350 mL, pH 8.5) with stirring. The mixture was transferred to a separatory funnel and separated. The aqueous phase was extracted once with dichloromethane (300 mL) and the combined organic phases were washed with triethylammonium bicarbonate buffer (350 mL, pH 8.5). The organic phase was dried over sodium sulfate, filtered, concentrated under vacuum, and the residue dried under vacuum. The crude material was purified by silica gel column chromatography using a step gradient of 0.5% triethylamnine in dichloromethane to 0.5% triethylamine in dichloromethane/methanol (9:1). The combined product fractions were evaporated to a foam and coevaporated twice with acetonitrile to remove trace triethylamine. Subsequently, the purified product was dissolved in dichloromethane (350 mL), washed twice with diazabicyclo[5.4.0]

undec-7-ene bicarbonate buffer (0.2 M, 350 mL, pH 8.7), dried over sodium sulfate, and evaporated to a foam. Prior to its use for solid phase synthesis the product was dried under high vacuum to give 5.5 g (90%) of the title compound. $^{31}$P-NMR (CDCl$_3$, external standard: 85% H$_3$PO$_4$): 3.77 ppm.

EXAMPLE 4
5'-O-DMT-2'-MOE-N-4-benzoyl-5-methyl-cytidine-3'-H-phosphonate

To a stirred solution of 1,2,4-triazole (8.29 g, 0.12 mole) and N-methylmorpholine (35.7 g, 0.353 mole) in dichloromethane (350 mL) phosphorus trichloride (4.85 g, 35.3 mmole) was added. The mixture was stirred for 30 minutes at room temperature and cooled down to 0° C. Subsequently 5'-O-DMT-2'-MOE-N-4-benzoylcytidine (5 g, 7.06 mmole) in dichloromethane (100 mL) was added dropwise over a period of 20 minutes. After stirring for another 20 minutes the mixture was allowed to warm up to room temperature and poured into aqueous triethylammonium bicarbonate buffer (350 mL, pH 8.5) with stirring. The mixture was transferred to a separatory funnel and separated. The aqueous phase was extracted once with dichloromethane (300 mL) and the combined organic phases were washed with aqueous triethylammonium bicarbonate buffer (350 mL, pH 8.5). The organic phase was dried over sodium sulfate, filtered, evaporated under vacuum and the resulting residue dried under high vacuum. The crude product was purified by silica gel column chromatography using a step gradient of 3% triethylamine in dichloromethane to 3% triethylamine in dichloromethane/methanol (9:1). The combined product fractions were evaporated to a foam and evaporated twice with acetonitrile to remove trace triethylamine. Subsequently the purified product was dissolved in dichloromethane (300 mL), washed twice with diazabicyclo[5.4.0] undec-7-ene bicarbonate buffer (300 mL, 0.2 M, pH 8.7), dried over sodium sulfate, and evaporated to a foam. Prior to its use for solid phase synthesis the product was dried under high vacuum to give 3.9 g (63%) of the title compound. $^{31}$P-NMR (CDCl$_3$, using 85% H$_3$PO$_4$ as an external standard): 3.76 ppm.

EXAMPLE 5
5'-O-DMT-2'-MOE-N-2-isobutyrylguanosine-3'-H-phosphonate

To a stirred solution of 1,2,4-triazole (11.84 g, 0.171 mole) and N-methylmorpholine (50.98 g, 0.504 mole) in dichloromethane (350 mL), phosphorus trichloride (6.92 g, 0.050 mole) was added. The mixture was stirred for 30 minutes at room temperature and cooled down to −20° C. 5'-O-DMT-2'-MOE-isobutyrylguanosine (6 g, 8.4 mmole) in dichloromethane (100 mL) was added dropwise over a period of 20 minutes. After stirring for another 20 minutes, the mixture was allowed to warm to room temperature and poured into aqueous triethylammonium bicarbonate buffer (350 mL, pH 8.5) with stirring. The mixture was transferred to a separatory funnel and separated. The aqueous phase was extracted once with dichloromethane (300 mL) and the combined organic phases were washed with aqueous triethylammonium bicarbonate buffer (350 mL, pH 8.5). After drying the organic phase over sodium sulfate, the solvent was evaporated and the crude product was dried under vacuum. The crude product was purified by silica gel column chromatography using a step gradient of 3% triethylamine in dichloromethane to 3% triethylamine in dichloromethane/methanol (9:1). The combined product fractions were evaporated to a foam and coevaporated twice with acetonitrile to remove trace triethylamine. Subsequently the purified product was dissolved in dichloromethane (50 mL), washed twice with diazabicyclo[5.4.0] undec-7-ene bicarbonate buffer (50 mL, 0.2 M, pH 8.7), dried over sodium sulfate, and evaporated to a foam. Prior to its use for solid phase synthesis the product was dried under high vacuum to give 0.8 g (12%) of the title compound. $^{31}$P-NMR (CDCl$_3$, external standard: 85% H$_3$PO$_4$): 3.68 ppm.

EXAMPLE 6
*Synthesis of Uniform* 2'-MOE-modified Phosphodiester Oligonucleotides The solid phase synthesis of a uniform phosphodiester oligonucleotide (SEQ ID No: 8, 20-mer) containing T, C, A and G nucleobases and having a 2'-methoxyethoxy (MOE) on each ribosyl sugar moiety, was performed on a 1 μmole scale using 5'-O-DMT-2'-MOE-5-methylcytidine-3'-succinyl CPG as the solid support. The synthesis cycle is described in the General Procedures above. After completion of synthesis the oligomer was oxidized using iodine (0.1 M) in pyridine/water (98:2) and washed with acetonitrile/pyridine (1:1) and acetonitrile. Deprotection and cleavage from the solid support was performed with aqueous ammonia (25–28%), as described in the General Procedures. Analysis of the crude product by electrospray mass spectrometry gave a relative molecular mass of 8023.5 (calculated mass: 8022.3).

EXAMPLE 7
Synthesis of 2'-MOE-modified Gapmer Phosphodiester Oligonucleotides The solid phase synthesis of a uniform phosphodiester oligonucleotide (SEQ ID No.: 2, 18-mer) containing T, C, A and G nucleobases and having a 2'-MOE group on 4 of the ribosyl sugar moieties at the 5' end of the oligonucleotide and on 5 ribosyl sugar moieties at the 3' end of the oligonucleotide was performed in a 1 μmole scale using 5'-O-DMT-2'-MOE-thymidine-3'-succinyl CPG as the solid support. The synthesis cycle is described in the General Procedures of Example 1. After synthesis the oligomer was oxidized using iodine (0.1 M) in pyridine/water (98:2) and washed with acetonitrile/pyridine (1:1) and acetonitrile. Deprotection and cleavage from the solid support was performed with aqueous ammonia (25–28%), as described in the General Procedures. Analysis of the crude product by electrospray mass spectrometry gave a relative molecular mass of 6435.5 (calculated mass: 6440.7).

EXAMPLE 8
Synthesis of 2'-MOE-modified Gapmer Phosphorothioate Oligonucleosides The solid phase synthesis of a uniform phosphorothioate oligonucleotide (SEQ ID No: 6, 19-mer) containing T, C, A and G nucleobases and having a 2'-MOE group on 5 of the ribosyl sugar moieties at the 5' end of the oligonucleotide and on 6 ribosyl sugar moieties at the 3' end of the oligonucleotide was performed in a 1 μmole scale using 5'-O-DMT-2'-MOE-thymidine-3'-succinyl CPG as the solid support. The synthesis cycle is described in the General Procedures. After completion of synthesis the oligomer was oxidized using elemental sulfur (5%) in carbon disulfide/pyridine/triethylamine (10:10:1) and washed with carbon disulfide, acetonitrile/pyridine (1:1) and acetonitrile. Deprotection and cleavage from the solid support was carried out with aqueous ammonia (25–28%), as described in the General Procedures. Analysis of the crude product by electrospray mass spectrometry gave a relative molecular mass of 6873.4 (calculated mass: 6874.8).

EXAMPLE 9

Synthesis of a 2'-MOE-modified Gapmer Oligomeric Compounds With a PO-PS-PO Mixed Backbone The solid phase synthesis of a gapped oligomer (SEQ ID No: 9, 20-mer) having phosphodiester internucleoside linkages on the 3' and the 5' ends with phosphorothioate internucleoside linkages between nucleosides 6–15 and having a 2'-MOE group on 6 of the ribosyl sugar moieties at each of the 5' and 3' ends of the gapped oligomer with internal ribosyl moieties being deoxyribo moieties, was performed on a 1 µmole scale using 5'-O-DMT-2'-MOE-adenosine-3'-succinyl CPG as the solid support. The synthesis cycle is described in the General Procedures of Example 1. After the first 5 couplings the oligomer was oxidized using 0.1 M DMAP in pyridine/carbontetrachloride/water (9:5:1). Prior to synthesis of the next segment, the solid support was thoroughly washed with acetonitrile/pyridine (1:1) and acetonitrile. After incorporation of nine additional H-phosphonate monomers (to give a 15-mer) the oligomer was oxidized using elemental sulfur (5%) in carbondisulfide/pyridine/triethylamine (10:10:1), as described in the General Procedures. Prior to synthesis of the next segment, the solid support was thoroughly washed with carbondisulfide, acetonitrile/pyridine (1:1) and acetonitrile. After completion of solid phase synthesis, the support-bound oligomer was finally treated with DMAP (0.1 M) in pyridine/carbontetrachloride/water (9:5:1) and washed with acetonitrile/pyridine (1:1) and acetonitrile. Deprotection and cleavage from the solid support was performed with aqueous ammonia (25–28%), as described in the General Procedures. Analysis of the crude product by electrospray mass spectrometry gave a relative molecular mass of 7425.9 (calculated mass: 7426.0).

EXAMPLE 10

Synthesis of a 2'-MOE-modified Gapmer Oligomeric Compounds With PN-PS-PN Mixed Backbone The solid phase synthesis of a gapmer oligomer (SEQ ID No: 4, 19-mer) having two dimethylaminoethyl (DMAE) phosphoramidate internucleoside linkages on the 3' and the 5' ends with phosphorothioate internucleoside linkages between nucleosides 4–16 and having a 2'-MOE group on 3 of the ribosyl sugar moieties at the 5' end and on 4 of the ribosyl sugar moieties at the 5' end of the oligomeric compound with internal ribosyl moieties being deoxyribo moieties was performed in a 1 µmole scale using 5'-O-DMT-2'-MOE-thymidine-3'-succinyl CPG as the solid support. The synthesis cycle is described in the General Procedures. After the first 2 couplings the oligomer was oxidized using 2-dimethylaminoethylamine (10%) in carbontetrachloride. Prior to synthesis of the next segment, the solid support was thoroughly washed with acetonitrile. After incorporation of fourteen additional H-phosphonate monomers (to give a 17-mer) the oligomer was oxidized using elemental sulfur (5%) in carbondisulfide/pyridine/triethylamine (10:10:1), as described in the General Procedures. Prior to synthesis of the next segment, the solid support was thoroughly washed with carbondisulfide, acetonitrilelpyridine (1:1) and acetonitrile. After completion of solid phase synthesis, the support-bound oligomer was finally treated with 2-dimethylaminoethylamine (10%) in carbontetrachloride. Deprotection and cleavage from the solid support was performed with aqueous ammonia (25–28%), as described in the General Procedures.

EXAMPLE 11

Synthesis of a 2'-MOE-modified Gapmer Oligomeric Compounds With PN-PO-PS-PO Mixed Backbone The solid phase synthesis of a gapmer oligomer (SEQ ID No: 10, 20-mer) having DMAE phosphoramidate internuleoside linkages between nucleosides 1–3 on the 5' end, phosphodiester internuleoside linkages between nucleosides 3 to 6 and 15 to 20, phosphorothioate internuleoside linkages between nucleosides 6 to 15, 2'-MOE group on 6 of the ribosyl sugar moieties at the 5' and the 3' end of the oligomeric compound, and with remaining ribosyl units being 2'-deoxy ribosyls, was performed in a 1 µmole scale using 5'-O-DMT-2'-MOE-adenosine-3'-succinyl CPG as the solid support. The synthesis cycle is described in the General Procedures of Example 1. After the first 5 couplings the oligomer was oxidized using triethylamine (0.1 M) in pyridine/carbontetrachloride/water (9:5:1). Prior to synthesis of the next segment, the solid support was thoroughly washed with acetonitrile/pyridine (1:1) and acetonitrile. After introduction of nine additional H-phosphonate monomers (to give an 15-mer) the oligomer was oxidized using elemental sulfur (5%) in carbondisulfide/pyridine/triethylamine (10:10:1), as described in the General Procedures. Prior to synthesis of the next segment, the solid support was thoroughly washed with carbondisulfide, acetonitrile/pyridine (1:1) and acetonitrile. After introduction of three additional H-phosphonate monomers (to give an 18-mer) the oligomer was oxidized using triethylamine (0.1 M) in pyridine/carbontetrachloride/water (9:5:1) and washed thoroughly with acetonitrile/pyridine (1:1) and then acetonitrile. After completion of solid phase synthesis, the support-bound oligomer was finally treated with 2-dimethylaminoethylamine (10%) in carbontetrachloride. Deprotection and cleavage from the solid support was performed with aqueous ammonia (25–28%), as described in the General Procedures. Analysis of the crude product by electrospray mass spectrometry gave a relative molecular mass of 7566.3 (calculated mass: 7566.3).

EXAMPLE 12

Synthesis of a 2'-MOE-modified Gapmer Oligomeric Compounds PN-PO-PS-PO-PN Mixed Backbone The solid phase synthesis of a gapmer oligomer (SEQ ID No: 11, 20-mer) having DMAE phosphoramidate internucleoside linkages between nucleosides 1–3 on the 5' end and 18–20 on the 3' end, phosphodiester internucleoside linkages between nucleosides 3 to 6 and 15 to 18, phosphorothioate internucleoside linkages between nucleosides 6 to 15, 2'-MOE group on 6 of the ribosyl sugar moieties at the 5' and the 3' end of the oligonucleotide, and with remaining ribosyl units being 2'-deoxy ribosyls was performed in a 1 µmole scale using 5'-O-DMT-2'-MOE-adenosine-3'-succinyl CPG as the solid support. The synthesis cycle is described in the General Procedures of Example 1. After the first 2 couplings the oligomer was oxidized, using 2-dimethylaminoethylamine (10%) in carbontetrachloride. Prior to synthesis of the next segment, the solid support was thoroughly washed with acetonitrile. After introduction of three additional H-phosphonate monomers (to give a 6-mer) the oligomer was oxidized using DMAP (0.1 M) in pyridine/carbontetrachloride/water (9:5:1) and thoroughly washed with acetonitrile/pyridine (1:1) and then acetonitrile. After introduction of nine additional H-phosphonate monomers (to give a 15-mer) the oligomer was oxidized using elemental sulfur (5%) in carbondisulfide/pyridine/triethylamine (10:10:1). Prior to synthesis of the next segment, the solid support was thoroughly washed with carbondisulfide, acetonitrile/pyridine (1:1), and acetonitrile. After introduction of three additional H-phosphonate monomers (to give an 18-mer) the oligomer was oxidized using DMAP (0.1 M) in pyridine/carbontetrachloride/water (9:5:1) and thoroughly washed with acetonitrile/pyridine (1:1) and acetonitrile. After completion of solid phase synthesis, the support-bound oligomer was treated with 2-dimethylaminoethylamine (10%) in carbontetrachloride. Deprotection and cleavage from the solid support was performed with aqueous ammonia (25–28%). Analysis of the crude product by electrospray mass spectrometry gave a relative molecular mass of 7704.6 (calculated mass: 7706.6).

Table I below shows the oligomeric compounds prepared according to the procedures described in the examples above.

TABLE 1

| SEQ ID NO. | Sequence 5'-3' | $Mr_{calc}$ | $Mr_{found}$ |
|---|---|---|---|
| 1 | T*T*T* T*T*T* T*T*T* T*T*T* T*T*T* T*T*T* T*T | 7429.5 | 7424.8 |
| 2 | T*T*T* T*GA CAC GGC AT*T* T*T*T* | 6440.7 | 6435.5 |
| 3 | T*$_N$T*$_N$T*$_N$ G$_S$A$_S$C$_S$ A$_S$C$_S$G$_S$ G$_S$C$_S$A$_S$ C$_S$C$_S$A$_S$ T*$_N$T*$_N$T*$_N$ T* | 6886.0 | n.a. |
| 4 | T*$_N$T*$_N$T*$_S$ G$_S$A$_S$C$_S$ A$_S$C$_S$G$_S$ G$_S$C$_S$A$_S$ C$_S$C$_S$A$_S$ T*$_S$T*$_N$T*$_N$ T* | 6777.8 | n.a. |
| 5 | T*$_S$T*$_S$T*$_S$ T*$_S$T*$_S$T*$_S$ T*$_S$T*$_S$T*$_S$ T*$_S$T*$_S$T*$_S$ T*$_S$T*$_S$T*$_S$ T*$_S$T*$_S$ | 6625.8 | 6626.0 |
| 6 | T*$_S$A*$_S$A*$_S$ T*$_S$T*$_S$C$_S$ G$_S$A$_S$A$_S$ C$_S$G$_S$G$_S$ C$_S$T*$_S$A*$_S$ T*$_S$A*$_S$A*$_S$T*$_S$ | 6874.8 | 6873.4 |
| 7 | T*$_S$A*$_S$A*$_S$ T*$_S$T*$_S$C$_S$ G$_S$A$_S$A$_S$ C$_S$G$_S$G$_S$ $_{CS}$A*$_S$A*$_S$ A*$_S$A*$_S$A*$_S$ T*$_S$ | 6892.9 | 6891.0 |
| 8 | T*C*T* G*A*G* T*A*G* C*A*G* A*G*G* A*G*C* T*C* | 8022.3 | 8023.5 |
| 9 | A*T*G* C*A*T*$_S$ T$_S$C$_S$T$_S$ G$_S$C$_S$C$_S$ C$_S$C$_S$C* A*A*G* G*A* | 7426.0 | 7425.9 |
| 10 | A*$_N$T*$_N$G* C*A*T*$_S$ T$_S$C$_S$T$_S$ G$_S$C$_S$C$_S$ C$_S$C$_S$C* A*A*G* G*A* | 7566.3 | 7566.3 |
| 11 | A*$_N$T*$_N$G* C*A*T*$_S$ T$_S$C$_S$T$_S$ G$_S$C$_S$C$_S$ C$_S$C$_S$C* A*A*G*$_N$ G*$_N$A* | 7706.6 | 7704.6 |

* = 2'-methoxyethoxy (MOE);
S = phosphorothioate internucleoside linkage; and
N = dimethylaminoethyl phosphoramidate internucleoside linkage.

EXAMPLE 13

General Procedure for the Synthesis of 2'-MOE-modified Gapmers With PN-PS-PN Mixed Backbone The solid phase synthesis of a 2'-MOE gapped oligomer having phosphoramidate internucleoside linkages at the 5' and 3' ends and internal deoxyribo moieties having phosphorothioate linkages is performed on a 1 mmole scale using a 5'-O-DMT-2'-nucleoside attached via a succinyl linking group to CPG as the solid support. The synthesis cycle is as described above in the general procedures of Example 1. After coupling a desired number of further nucleosides to the solid support bound nucleoside the resulting oligomer is oxidized using 2-dimethylarninoethylamine (10%) in carbon tetrachloride. Prior to further elongation the solid support is washed with acetonitrile. After coupling of a desired number of further nucleosides oxidation to for phosphorothioate internuleoside linkages is performed using elemental sulfur (5%) and 4-(dimethylamino)pyridine (0.1 M) in carbon disulfide/pyridine (1:1). The solid support is again washed with carbon disulfide, acetonitrile/pyridine (1:1) and acetonitrile. After addition of a desired number of further nucleosides, the support-bound oligomer is treated with 10% 2-dimethylaminoethylamine in carbon tetrachloride. Deprotection and cleavage from the solid support is performed with aqueous ammonia (25–28%) to give the desired oligomeric compound.

EXAMPLE 14

General Procedure for the Synthesis of 2'-MOE-modified Gapmers With PBH$_3$-PS-PBH$_3$ Mixed Backbone The solid phase synthesis of a 2'-MOE gapped oligomer having boranophosphate internucleoside linkages at the 5' and 3' ends and internal deoxyribo moieties having phosphorothioate linkages is performed on a 1 mmole scale using a 5'-O-DMT-2'-nucleoside attached via a succinyl linking group to CPG as the solid support. The synthesis cycle is as described above in the general procedures of Example 1. After coupling a desired number of further nucleosides to the solid support bound nucleoside the resulting oligomeric compound is treated with N,O-bis(trimethylsilyl)trifluoroacetamide (0.3 M) in dry tetrahydrofuran for 30 minutes and washed with tetrahydrofuran. Subsequently, the support-bound oligomer is treated with borane-N,N-diisopropylethylamine (0.5 M) complex in dry tetrahydrofuran for 2 hours at room temperature. Prior to synthesis of the next segment, the solid support is washed with acetonitrile. After coupling of a desired number of further nucleosides, the H-phosphonate internucleoside linkages are oxidized to phosphorothioate internucleoside linkages using elemental sulfur (5%) and 4-(dimethylamino)pyridine (0.1 M) in carbon disulfide/pyridine (1:1). Prior to elongation of the oligomer the solid support is washed with carbon disulfide, acetonitrile/pyridine (1:1) and acetonitrile. After coupling of a desired number of further nucleosides the H-phosphonate internucleoside linkages are treated at room temperature with N,O-bis(trimethylsilyl)trifluoroacetamide (0.3 M) in dry tetrahydrofuran for 30 minutes and washed with tetrahydrofuran. Subsequently, the support-bound oligomer is treated with 0.5 M borane-N,N-diisopropylethylamine complex in dry tetrahydrofuran for 2 hours at room temperature. Deprotection and cleavage from the solid support is performed with aqueous ammonia (25–28%).

Biological Assays

Procedure A

ICAM-1 Expression

Targeted oligomeric compounds were prepared and assayed using HUVEC cells to determine their ability to inhibit the expression of ICAM-1. HUVEC cells were washed three times with Opti-MEM (Life Technologies, Inc.) that was prewarmed to 37° C. Oligomeric compounds were premixed with Lipofectin (10 μg/mL, Life Technologies, Inc.) in Opti-MEM, serially diluted to the desired concentrations, and applied to washed cells. Basal and untreated (no oligomeric compounds added) control cells were also treated with Lipofectin. Cells were incubated for 4 hours at 37° C., at which time the medium was removed and replaced with standard growth medium with or without TNF-a (5mg/mL, R&D Systems). Incubation at 37° C. was continued for different times as indicated below.

A fluorescence-activated cell sorter was used to quantitate ICAM-1 protein expression. The cells were removed from the plate surface by brief trypsinization with trypsin (0.25%) in PBS. Trypsin activity was quenched with a solution of bovine serum albumin (2%) and sodium azide (0.2%) in PBS (+Mg/Ca). Cells were pelleted by centrifugation (1000 rpm, Beckman GPR centrifuge), resuspended in PBS, and stained with ICAM-1 specific antibody (3 μL/105 cells), CD54-PE (Pharmingin). The antibodies were incubated with the cells for 30 minutes at 4° C. in the dark, under gentle agitation. Cells were washed by centrifugation procedures and then resuspended in FacsFlow buffer (0.3 mL, Becton Dickinson) with formaldehyde (0.5%, Polysciences).

Expression of cell surface ICAM-1 was determined by flow cytometry using a Becton Dickinson FACScan. The percentage of ICAM-1 expression in the control was calculated as follows: [(oligomeric compound-treated ICAM-1 value)—(basal ICAM-1 value)/(non-treated ICAM-1 value)—(basal ICAM-1 value))]. In one study, 2'-O-(2-methoxy)ethyl-modified anti-intercellular adhesion molecule 1 (ICAM-1) oligomeric compounds were shown to selectively increase the ICAM-1 mRNA level and inhibit formation of the ICAM-1 translation initiation complex in human umbilical vein endothelial cells (Baker et al., The Journal of Biological Chemistry, 1997, 272, 11994–12000).

ICAM-1 expression data reveal that the uniform phosphorothioate MOE oligomer T*C*T* G*A*G* T*A*G* C*A*G* (SEQ ID NO: 12 ; *=2'-methoxyethoxy (MOE)) sequence synthesized by amidite chemistry and the same compound synthesized by H-phosphonate chemistry are efficacious in HUVEC cells in controlling ICAM-1 expression. The oligomers are presumably working by a direct binding RNase H independent mechanism. Both compounds synthesized from different chemistries display dose response in inhibiting ICAM-1 expression between 3 and 100 nM range.

Procedure B c-raf MRNA Expression in A549 Cells

Gapmers designed in this study are based on the parent sequence of ATG CAT TCT GCC CCC AAG GA (SEQ ID NO:9) which is a uniform deoxy phosphorothioate. This sequence is an antisense oligomeric compound targeted to mouse c-raf c-raf m-RNA expression assay was carried out according to a reported procedure (Monia et al., Nature Medicinek, 1996, 2, 668). Human A549 lung carcinoma cells were obtained from the American Type Tissue Collection. These were grown in Dulbecco's modified Eagle's medium containing 1 g of glucose/liter (DMEM) and FCS (10%) and routinely passaged when 90–95% confluent.

Assay for Oligonucleoside Inhibition of c-raf Protein Synthesis: A549 cells were plated in 6-well plates (Falcon Labware, Lincoln Park, N.J.) and 24–48 hours later (when 80–90% confluent) treated with 1 μM phorbol 12,13-dibutyrate (PDBu) for 18 hours. This procedure removes greater than 75% of immunoreactive c-raf protein from the cells. Cells were then washed three times with DMEM (3 mL) (to remove PDBu), and DMEM (1 mL) containing DOTMA/DOPE solution (20 μg/mL, LipofectinR, Bethesda Research Laboratories) was added. Oligonucleoside gapmers were then added to the required concentration (for our initial screen, 1 μM) from a 10 μM stock solution, and the two solutions were mixed by swirling of the dish. The cells were incubated at 37° C. for 4 hours, washed once with DMEM+FCS (10%) to remove the DOTMA/DOPE solution, and then additional DMEM (3 mL)+10% FCS was added and the cells were allowed to recover for another 10 hours. Total RNA is prepared 24 hours after the experiment and analyzed for c-raf and G3PDH mRNA levels after normalization to G3PDH mRNA.

Results: Gapped oligomeric compounds (SEQ ID NO: 9, 10 and 11, Table 1) inhibit c-raf mRNA expression in A549 cells in a dose dependent manner between 50–400 nM range. The duration of the effect in reducing c-raf expression is much longer for P═N containing Gapmers as expected from the improved nuclease resistance.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method of preparing an oligomeric compound of formula:

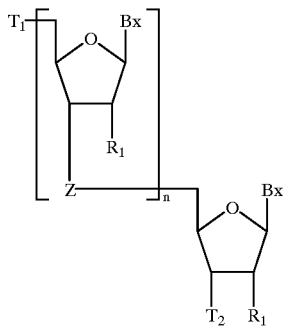

wherein:
each Z is, independently, a phosphodiester, phosphorothioate, phosphoramidate or boranophosphate internucleoside linkage;
each $T_1$ and $T_2$ is, independently, hydroxyl or a protected hydroxyl;
Bx is a heterocyclic base moiety;
each $R_1$ is, independently, H, hydroxyl, a protected hydroxyl, a 2'-substituent group or a protected 2'-substituent group; and
n is an integer greater than 1; provided that at least one of said Z is phosphodiester and at least another of said Z is a phosphorothioate, phosphoramidate or boranophosphate internucleoside linkage;
comprising the steps of:
(a) providing a compound of formula:

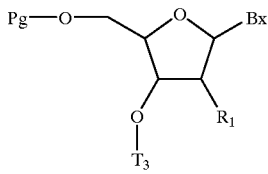

wherein:
Pg is an acid labile hydroxyl protecting group; and
$T_3$ is a base labile hydroxyl protecting group or a covalent attachment to a solid support;
(b) deblocking said acid labile hydroxyl protecting group to form a deblocked hydroxyl group;
(c) treating said deblocked hydroxyl group with a further compound having the formula:

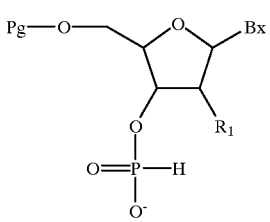

and a condensing reagent in a solvent under conditions of time, temperature and pressure effective to form an extended compound having an added H-phosphonate internucleoside linkage;
(d) optionally treating said extended compound with a capping agent to form a capped compound;
(e) optionally treating said capped compound with a silylating agent to give a silylated compound;
(f) optionally repeating steps (b), (c), (d) and (e);
(g) treating said extended compound, said capped compound, or said silylated compound with an oxidizing solution inert to a phosphodiester, phosphoramidate, phosphorothioate or boranophosphate internucleoside linkage, thereby oxidizing said H-phosphonate internucleoside linkages to phosphodiester, phosphorothioate, phosphoramidate or boranophosphate internucleoside linkages;
(h) optionally repeating steps (b), (c), (d), (e), (f), and (g) to form a protected oligomeric compound; and
(i) treating said protected oligomeric compound with a deblocking solution to form said oligomeric compound.

2. The method of claim 1 wherein $R_1$ is a 2'-substituent group.

3. The method of claim 2 wherein said 2'-substituent group is —O—$CH_2CH_2$—O—$CH_3$, —O—$CH_2CH_2$—O—$N(R_6)(R_7)$ or —O—$CH_2CH_2$—$_{O-CH_2}$$CH_2$—$N(R_6)(R_7)$, wherein each of $R_6$ and $R_7$ is, independently, H or $C_1$–$C_{10}$ alkyl.

4. The method of claim 3 wherein each $R_6$ and $R_7$ is —$CH_3$.

5. The method of claim 1 wherein said silylating agent is chlorotrimethylsilane, N,O-bis-(trimethylsilyl)acetamide, heptamethyldisilazane or N,O-bis-(trimethylsilyl)-trifluoroacetamide.

6. The method of claim 1 wherein said condensing reagent is an acid chloride, a chlorophosphonate, a carbonate, a carbonium type compound or a phosphonium type compound.

7. The method of claim 6 wherein said condensing reagent is pivaloyl chloride, adamantyl chloride, 2,4,6- triisopropylbenzenesulfonyl chloride, 2-chloro-5,5-dimethyl-2-oxo-1,3,2-dioxaphosphinane, diphenyl phosphorochloridate, bis(2-oxo-3-oxazolidinyl)phosphinic chloride, bis(pentafluorophenyl)carbonate, 2-(1H-benzotriazole-1-yl)-1,1,3,3-tetramethyluronium hexafluorophosphate, O-(azabenzotriazol-1-yl)-1,1,3,3-tetramethyl uronium hexafluorophosphate, 6-(trifluoromethyl)benzotriazol-1-yl-oxy-tris-pyrrolidino-phosphonium hexafluorophosphate, bromo-tris-pyrrolidino-phosphonium hexafluorophosphate, benzotriazole-1-yl-oxy-tris-pyrrolidino-phosphonium hexafluorophosphate or 2-(benzotriazol-1-yloxy)-1,3-dimethyl-2-pyrrolidin-1-yl-1,3,2-diazapholidinium hexafluorophosphate.

8. The method of claim 1 wherein said mixed backbone oligomeric compound comprises contiguous regions of said phosphodiester and said phosphorothioate moieties.

9. The method of claim 1 wherein said mixed backbone oligomeric compound comprises contiguous regions of said phosphodiester and said phosphoramidate moieties.

10. The method of claim 1 wherein said mixed backbone oligomeric compound comprises contiguous regions of nucleosides having one or more of said phosphorothioate, phosphoramidate and boranophosphate internucleoside linkages in addition to at least one of said phosphodiester internucleoside linkage.

11. The method of claim 1 wherein said acid labile hydroxyl protecting group is dimethoxytrityl, monomethoxy trityl, trityl or 9-phenyl-xanthene.

12. The method of claim 1 wherein said heterocyclic base moiety is a purine or a pyrimidine.

13. The method of claim 12 wherein said purine or pyrimidine is adenine, cytosine, 5-methylcytosine, thymine, uracil, guanine or 2-aminoadenine.

14. The method of claim 1 wherein $T_3$ is a covalent attachment to a solid support.

15. The method of claim 1 wherein said mixed backbone oligomeric compound comprises from about 5 to about 50 nucleosides.

16. The method of claim 1 wherein said mixed backbone oligomeric compound comprises from about 8 to about 30 nucleosides.

17. The method of claim 1 wherein said mixed backbone oligomeric compound comprises from about 15 to about 25 nucleosides.

18. The method of claim 1 wherein said oxidizing solution comprises an oxidizing agent, an aprotic organic solvent, a base and water.

19. The method of claim 18 wherein said oxidizing agent is carbon tetrachloride, carbon tetrabromide, N-chlorosuccinimide or N-bromosuccinimide.

20. The method of claim 18 wherein said aprotic organic solvent is pyridine, acetonitrile or dimethylformamide.

21. The method of claim 18 wherein said base is a tertiary amine having a pKa value from about 9 to about 12.

22. The method of claim 21 wherein said tertiary amine is 4-(dimethylamino)pyridine, triethylamine or N,N-diisopropylethylamine.

23. The method of claim 18 wherein said oxidizing solution comprises carbon tetrachloride, 4-(dimethylamino)pyridine in pyridine and water.

24. The method of claim 18 wherein said oxidizing solution comprises from about 18% to about 45% oxidizing agent, from about 2% to about 15% water, from about 40% to about 80% aprotic organic solvent and from about 0.01 M to about 0.8 M base dissolved in said aprotic organic solvent.

25. The method of claim 18 wherein said oxidizing solution comprises from about 26% to about 40% oxidizing agent, from about 4% to about 10% water, from about 50% to about 70% aprotic organic solvent and from about 0.04 M to about 0.4 M base dissolved in said aprotic organic solvent.

26. The method of claim 18 wherein said oxidizing solution comprises about 33% oxidizing agent, about 7% water, about 60% aprotic organic solvent and from about 0.05 M to about 0.2 M base dissolved in said aprotic organic solvent.

27. The method of claim 1 wherein said oxidizing solution comprises an oxidizing agent, a solvent that dissolves said oxidizing agent, an aprotic organic solvent and a base.

28. The method of claim 27 wherein said base is a tertiary amine having a pKa value from about 9 to about 12.

29. The method of claim 28 wherein said tertiary amine is 4-(dimethylamino)pyridine, triethylamine or N,N-diisopropylethylamine.

30. The method of claim 27 wherein said aprotic organic solvent is pyridine, acetonitrile or dimethylformamide.

31. The method of claim 27 wherein said solvent that dissolves said oxidizing agent is carbon disulfide.

32. The method of claim 27 wherein said oxidizing solution comprises elemental sulfur, carbon disulfide, pyridine and 4-(dimethylamino)pyridine.

33. The method of claim 27 wherein said oxidizing solution comprises from about 1% to about 15% oxidizing agent, about 40% to about 60% solvent that will solubilize said oxidizing agent, from about 40% to about 60% aprotic organic solvent and from about 0.01 M to about 0.8 M base dissolved in said aprotic organic solvent.

34. The method of claim 27 wherein said oxidizing solution comprises from about 1% to about 10% oxidizing agent, about 40% to about 60% solvent that will solubilize said oxidizing agent, from about 40% to about 60% aprotic organic solvent and from about 0.02 M to about 0.5 M base dissolved in said aprotic organic solvent.

35. The method of claim 27 wherein said oxidizing solution comprises from about 3% to about 8% oxidizing agent, about 40% to about 60% solvent that will solubilize said oxidizing agent, from about 40% to about 60% aprotic organic solvent and from about 0.04 M to about 0.1 M base dissolved in said aprotic organic solvent.

36. The method of claim 27 wherein said oxidizing solution comprises about 5% elemental sulfur and about 0.1 M 4-(dimethylamino)pyridine in a mixture of carbon disulfide and pyridine.

37. The method of claim 1 wherein said oxidizing solution comprises a primary or secondary amine and oxidizing agent.

38. The method of claim 37 wherein said oxidizing solution comprises from about 1% to about 10% of said primary or secondary amine and from about 90% to about 99% of said oxidizing agent.

39. The method of claim 37 wherein said oxidizing solution comprises about 2% to about 5% of said primary or secondary amine in said oxidizing agent.

40. The method of claim 37 wherein said oxidizing solution comprises about 3% primary or secondary amine in carbon tetrachloride.

* * * * *

SEQUENCE LISTING

```
<160> NUMBER OF SEQ ID NOS:  12

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: 2'-methoxyethoxy (MOE)
<223> OTHER INFORMATION: Description of Artificial Sequence:  Novel
      Sequence

<400> SEQUENCE: 1
```
tttttttttt tttttttttt                                                           20

<210> SEQ ID NO 2
<211> LENGTH: 18
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: 2'-methoxyethoxy (MOE)
<221> NAME/KEY: misc_feature
<222> LOCATION: (14)..(18)
<223> OTHER INFORMATION: 2'-methoxyethoxy (MOE)
<223> OTHER INFORMATION: Description of Artificial Sequence: Novel
      Sequence

<400> SEQUENCE: 2
ttttgacacg gcattttt                                                             18

<210> SEQ ID NO 3
<211> LENGTH: 19
<212> TYPE: DNA
<213> ORGANISM: Artificial Sequence
<220> FEATURE:
<221> NAME/KEY: misc_feature
<222> LOCATION: (1)..(3)
<223> OTHER INFORMATION: 2'-methoxyethoxy (MOE); modified linkage
<221> NAME/KEY: misc_feature
<222> LOCATION: (4)..(15)
<223> OTHER INFORMATION: modified linkage
<221> NAME/KEY: misc_feature
<222> LOCATION: (16)..(18)
<223> OTHER INFORMATION: 2'-methoxyethoxy (MOE); modified linkage
<221> NAME/KEY: misc_feature
<222> LOCATION: (19)
<223> OTHER INFORMATION: 2'-methoxyethoxy (MOE)
<223> OTHER INFORMATION: Description of Artificial Sequence: Novel
      Sequence

<400> SEQUENCE: 3
tttgacacgg caccatttt                                                            19

<210> SEQ ID NO 4
<211> LENGTH: 19
<212> TYPE: DNA
<213> ORGANISM: Artificial Sequence
<220> FEATURE:
<221> NAME/KEY: misc_feature
<222> LOCATION: (1)..(3)
<223> OTHER INFORMATION: 2'-methooxyethoxy (MOE); modified linkage
<221> NAME/KEY: misc_feature
<222> LOCATION: (4)..(15)
<223> OTHER INFORMATION: modified linkage
<221> NAME/KEY: misc_feature
<222> LOCATION: (16)..(18)
<223> OTHER INFORMATION: 2'-methoxyethoxy (MOE); modified linkage
<221> NAME/KEY: misc_feature
<222> LOCATION: (19)
<223> OTHER INFORMATION: 2'-methoxyethoxy (MOE)
<223> OTHER INFORMATION: Description of Artificial Sequence: Novel
      Sequence

<400> SEQUENCE: 4
tttgacacgg caccatttt                                                            19

<210> SEQ ID NO 5
<211> LENGTH: 17
<212> TYPE: DNA
<213> ORGANISM: Artificial Sequence
<220> FEATURE:
<221> NAME/KEY: misc_feature

```
<222> LOCATION: (1)..(17)
<223> OTHER INFORMATION: 2'-methoxyethoxy (MOE); modified linkage
<223> OTHER INFORMATION: Description of Artificial Sequence: Novel
      Sequence

<400> SEQUENCE: 5
tttttttttt tttttt                                                    17

<210> SEQ ID NO 6
<211> LENGTH: 19
<212> TYPE: DNA
<213> ORGANISM: Artificial Sequence
<220> FEATURE:
<221> NAME/KEY: misc_feature
<222> LOCATION: (1)..(5)
<223> OTHER INFORMATION: 2'-methoxyethoxy (MOE); modified linkage
<221> NAME/KEY: misc_feature
<222> LOCATION: (6)..(13)
<223> OTHER INFORMATION: modified linkage
<221> NAME/KEY: misc_feature
<222> LOCATION: (14)..(19)
<223> OTHER INFORMATION: 2'-methoxyethoxy (MOE); modified linkage
<223> OTHER INFORMATION: Description of Artificial Sequence: Novel
      Sequence

<400> SEQUENCE: 6
taattcgaac ggctataat                                                 19

<210> SEQ ID NO 7
<211> LENGTH: 19
<212> TYPE: DNA
<213> ORGANISM: Artificial Sequence
<220> FEATURE:
<221> NAME/KEY: misc_feature
<222> LOCATION: (1)..(5)
<223> OTHER INFORMATION: 2'-methoxyethoxy (MOE); modified linkage
<221> NAME/KEY: misc_feature
<222> LOCATION: (6)..(13)
<223> OTHER INFORMATION: modified linkage
<221> NAME/KEY: misc_feature
<222> LOCATION: (14)..(19)
<223> OTHER INFORMATION: 2'-methoxyethoxy (MOE); modified linkage
<223> OTHER INFORMATION: Description of Artificial Sequence: Novel
      Sequence

<400> SEQUENCE: 7
taattcgaac ggcaaaaat                                                 19

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: 2'-methoxyethoxy (MOE)
<223> OTHER INFORMATION: Description of Artificial Sequence: Novel
      Sequence

<400> SEQUENCE: 8
tctgagtagc agaggagctc                                                20

<210> SEQ ID NO 9
<211> LENGTH: 20
<212> TYPE: DNA
<213> ORGANISM: Artificial Sequence
<220> FEATURE:
<221> NAME/KEY: misc_feature
<222> LOCATION: (1)..(5)
<223> OTHER INFORMATION: 2'-methoxyethoxy (MOE)
<221> NAME/KEY: misc_feature
```

```
<222> LOCATION: (6)
<223> OTHER INFORMATION: 2'-methoxyethoxy (MOE); modified linkage
<221> NAME/KEY: misc_feature
<222> LOCATION: (7)..(14)
<223> OTHER INFORMATION: modified linkage
<221> NAME/KEY: misc_feature
<222> LOCATION: (15)..(20)
<223> OTHER INFORMATION: 2'-methoxyethoxy (MOE)
<223> OTHER INFORMATION: Description of Artificial Sequence:  Novel
      Sequence

<400> SEQUENCE: 9
atgcattctg cccccaagga                                                    20

<210> SEQ ID NO 10
<211> LENGTH: 20
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: 2'-methoxyethoxy (MOE); modified linkage
<221> NAME/KEY: misc_feature
<222> LOCATION: (3)..(5)
<223> OTHER INFORMATION: 2'-methoxyethoxy (MOE)
<221> NAME/KEY: misc_feature
<222> LOCATION: (6)
<223> OTHER INFORMATION: 2'-methoxyethoxy (MOE); modified linkage
<221> NAME/KEY: misc_feature
<222> LOCATION: (7)..(14)
<223> OTHER INFORMATION: modified linkage
<221> NAME/KEY: misc_feature
<222> LOCATION: (15)..(20)
<223> OTHER INFORMATION: 2'-methoxyethoxy (MOE)
<223> OTHER INFORMATION: Description of Artificial Sequence:  Novel
      Sequence

<400> SEQUENCE: 10
atgcattctg cccccaagga                                                    20

<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: 2'-methoxyethoxy (MOE); modified linkage
<221> NAME/KEY: misc_feature
<222> LOCATION: (3)..(5)
<223> OTHER INFORMATION: 2'-methoxyethoxy (MOE)
<221> NAME/KEY: misc_feature
<222> LOCATION: (6)
<223> OTHER INFORMATION: 2'-methoxyethoxy (MOE); modified linkage
<221> NAME/KEY: misc_feature
<222> LOCATION: (7)..(14)
<223> OTHER INFORMATION: modified linkage
<221> NAME/KEY: misc_feature
<222> LOCATION: (15)..(17)
<223> OTHER INFORMATION: 2'-methoxyethoxy (MOE)
<221> NAME/KEY: misc_feature
<222> LOCATION: (18)..(19)
<223> OTHER INFORMATION: 2'-methoxyethoxy (MOE); modified linkage
<221> NAME/KEY: misc_feature
<222> LOCATION: (20)
<223> OTHER INFORMATION: 2'-methoxyethoxy (MOE)
<223> OTHER INFORMATION: Description of Artificial Sequence:  Novel
      Sequence

<400> SEQUENCE: 11
atgcattctg cccccaagga                                                    20

<210> SEQ ID NO 12
```

```
-continued

<211> LENGTH: 12
<212> TYPE: DNA
<213> ORGANISM: Artificial Sequence
<220> FEATURE:
<221> NAME/KEY: misc_feature
<222> LOCATION: (1)..(12)
<223> OTHER INFORMATION: 2'-methoxyethoxy (MOE)
<223> OTHER INFORMATION: Description of Artificial Sequence:  Novel
      Sequence

<400> SEQUENCE: 12
tctgagtagc ag                                                         12
```